(12) United States Patent
Ohki et al.

(10) Patent No.: US 12,178,839 B2
(45) Date of Patent: Dec. 31, 2024

(54) ANTI-OBESITY AGENT, POLLAKIURIA IMPROVING AGENT, AND AUTONOMIC NERVOUS ACTIVITY REGULATOR

(71) Applicant: ASAHI GROUP HOLDINGS, LTD., Tokyo (JP)

(72) Inventors: Kohji Ohki, Ibaraki (JP); Koki Sato, Kanagawa (JP); Kazuhito Ohsawa, Kanagawa (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 228 days.

(21) Appl. No.: 17/288,197

(22) PCT Filed: Oct. 17, 2019

(86) PCT No.: PCT/JP2019/040809
§ 371 (c)(1),
(2) Date: Apr. 23, 2021

(87) PCT Pub. No.: WO2020/085179
PCT Pub. Date: Apr. 30, 2020

(65) Prior Publication Data
US 2021/0401928 A1 Dec. 30, 2021

(30) Foreign Application Priority Data
Oct. 26, 2018 (JP) ................. 2018-202084

(51) Int. Cl.
*A61K 38/10* (2006.01)
*A61P 3/04* (2006.01)
*A61P 13/10* (2006.01)

(52) U.S. Cl.
CPC ............... *A61K 38/10* (2013.01); *A61P 3/04* (2018.01); *A61P 13/10* (2018.01)

(58) Field of Classification Search
CPC ...... A61K 38/10; A61K 38/018; A61K 38/04; A61K 38/00; A61K 38/1709; A61K 35/747; A61P 13/10; A61P 3/04; A61P 13/00; A61P 25/28; A61P 25/00; A61P 43/00
See application file for complete search history.

(56) References Cited

U.S. PATENT DOCUMENTS

| | | | | |
|---|---|---|---|---|
| 8,569,241 B2 * | 10/2013 | Ohsawa | .................. | A61P 43/00 514/17.7 |
| 9,523,109 B2 * | 12/2016 | Uchida | .............. | C07K 14/4732 |
| 10,086,034 B2 | 10/2018 | Thor et al. | | |
| 10,172,899 B2 | 1/2019 | Park et al. | | |
| 2010/0021444 A1 * | 1/2010 | Kawakami | ................ | A23L 2/52 435/252.9 |
| 2012/0277160 A1 | 11/2012 | Ohsawa et al. | | |
| 2016/0175382 A1 | 6/2016 | Thor et al. | | |
| 2017/0095520 A1 | 4/2017 | Park et al. | | |
| 2018/0055902 A1 | 3/2018 | Park et al. | | |

FOREIGN PATENT DOCUMENTS

| | | |
|---|---|---|
| AU | 2011327288 | 5/2012 |
| EP | 2 520 308 | 11/2012 |
| EP | 2 735 616 | 5/2014 |
| JP | 2004-323519 | 11/2004 |
| JP | 2005-160356 | 6/2005 |
| JP | 2006-265142 | 10/2006 |
| JP | 2006-328056 | 12/2006 |
| JP | 3164015 | 11/2010 |
| JP | 2013-005757 | 1/2013 |
| JP | 2014-084283 | 5/2014 |
| JP | 2016-527271 | 9/2016 |
| JP | 6063543 | 1/2017 |
| JP | 2017-513822 | 6/2017 |
| JP | 2017-214342 | 12/2017 |
| WO | 2012/029199 | 3/2012 |
| WO | 2012/063826 | 5/2012 |

OTHER PUBLICATIONS

Morr, C.V., Chemistry of Milk Proteins in Food Processing, Journal of Dairy Sciences; 58(7): 977-983. (Year: 1974).*
Maughan et al, A randomized trial to assess the potential of different beverages to affect hydration status: development of a beverage hydration index, Am J Clin Nutr; 103:717-23. (Year: 2016).*
Extended European Search Report issued Jun. 14, 2022 in corresponding European Patent Application No. 19877309.5.
Kazuhito Ohsawa et al., "*Lactobacillus helveticus*-fermented milk containing lactononadecapeptide (NIPPLTQTPVWPPFLQPE) improves cognitive function in healthy middle-aged adults: a randomised, double-blind, placebo-controlled trial", International Journal of Food Sciences and Nutrition, vol. 69, No. 3, pp. 369-376, Aug. 18, 2017.
Yan Jin et al., "Peptide profiling and the bioactivity character of yogurt in the simulated gastrointestinal digestion", Journal of Proteomics, vol. 141, pp. 24-46, Apr. 20, 2016.
International Search Report issued Nov. 26, 2019, in International (PCT) Application No. PCT/JP2019/040809.
Nakamura, "Physiological effects of fermented milk and calpis sour milk", Food Processing and Ingredients, vol. 34, 1999, pp. 12-14.
Aoi et al., "Inhibitory effect of fermented milk on delayed-onset muscle damage after exercise", Journal of Nutritional Biochemistry, vol. 18, 2007, pp. 140-145.
Iwasa et al., "Fermented milk improves glucose metabolism in exercise-induced muscle damage in young healthy men", Nutrition Journal, vol. 12, 2013, No. 83.

\* cited by examiner

*Primary Examiner* — Lianko G Garyu
*Assistant Examiner* — John Cronin
(74) *Attorney, Agent, or Firm* — Wenderoth, Lind & Ponack, L.L.P.

(57) ABSTRACT

[Problem] The purpose of the present invention is to provide a novel technique associated with anti-obesity improvement. [Solution] The present invention relates to an anti-obesity agent comprising lactononadecapeptide (LNDP, Asn-Ile-Pro-Pro-Leu-Thr-Gln-Thr-Pro-Val-Val-Val-Pro-Pro-Phe-Leu-Gln-Pro-Glu) or a salt thereof. The present invention also relates to a pollakiuria improving agent and an autonomic nerve activity regulator each comprising LNDP.

2 Claims, 6 Drawing Sheets

Specification includes a Sequence Listing.

AVERAGE VALUE ± STANDARD ERROR
* P < 0.05 VS. PLACEBO (WILCOXON SIGNED RANK TEST)

AVERAGE VALUE ± STANDARD ERROR
* P < 0.05 VS. PLACEBO FOOD (WILCOXON SIGNED RANK TEST)

SEQUENCE LISTING

<160> NUMBER OF SEQ ID NOS: 1

<210> SEQ ID NO 1
<211> LENGTH: 19
<212> TYPE: PRT
<213> ORGANISM: artificial
<220> FEATURE:
<223> OTHER INFORMATION: functional peptide

<400> SEQUENCE: 1

Asn Ile Pro Pro Leu Thr Gln Thr Pro Val Val Val Pro Pro Phe Leu
1               5                   10                  15

Gln Pro Glu

ANTI-OBESITY AGENT, POLLAKIURIA IMPROVING AGENT, AND AUTONOMIC NERVOUS ACTIVITY REGULATOR

TECHNICAL FIELD

The present invention relates to an anti-obesity agent, a pollakiuria improving agent, an autonomic nervous activity regulator, and the like.

BACKGROUND ART

The quality of life (QOL) may deteriorate at the present time due to aging or change in lifestyle. Lifestyle-related diseases including visceral obesity and urinary disorder, and the like background the deterioration of the QOL, and the disturbance of autonomic nervous activity may participate in these.

Specifically modern people, for example, have expanded opportunities to ingest high fat diet, and become increasingly lacking in exercise with change in the lifestyle of modern people in recent years. In such modern lifestyle, the balance between calorie intake and consumption tilts to the intake side, so that fat is accumulated, and obesity, which is in its excessive state, occurs easily. Especially visceral obesity directly causes metabolic syndrome.

The progress of such a state of obesity spoils healthy and comfortable life markedly.

Therefore, anti-obesity agents based on body fat decomposition promoting effect, and the like have been proposed, and, for example, capsaicin contained in red peppers (Patent Literature 1), plant bodies of plants belonging to Brassicaceae (Patent Literature 2), and the like are known.

For example, as for urinary disorder, subject persons suffering from urinary disorder are increasing, and pollakiuria is known as one thereof. Pollakiuria is an event in which since urination occurs before the original bladder's capacity for storing urine is utilized, the frequency of urination increases. Pollakiuria is stressful in daily life, and pollakiuria during the nighttime reduces the quality and quantity of sleep, and spoils healthy and comfortable life.

As a pollakiuria improving substance, anticholinergic drugs and an adrenaline β3 receptor agonist have already been marketed for drugs, and saw palmetto has already been marketed for supplements. Besides, as substances derived from foods, Patent Literature 3 discloses *Piper longum*, Patent Literature 4 discloses linear saturated fatty acids having 6 to 12 carbon atoms in edible oils, Patent Literature 5 discloses banana extract, Patent Literature 6 discloses *Perilla* leaves, and Patent Literature 7 discloses pumpkin seeds.

Patent Literature 8 discloses amino acid-substituted and modified peptides of neurokinin, which are a neuropeptide, as urinary incontinence preventive drugs by peptide-based substances.

CITATION LIST

Patent Literature

Patent Literature 1
JP2006-265142
Patent Literature 2
JP2006-328056
Patent Literature 3
JP2017-513822
Patent Literature 4
JP2017-214342
Patent Literature 5
Japanese Patent No. 6063543
Patent Literature 6
JP2005-160356
Patent Literature 7
Japanese Utility Model Registration No. 3164015
Patent Literature 8
JP2016-527271

SUMMARY OF INVENTION

Technical Problem

An object of the present invention is to provide new technology relating to anti-obesity.

Solution to Problem

Although drugs which enable improving obesity also exist, the drugs have side effects, and the development of a secure and safe functional component having an excellent effect and derived from foods has therefore been waited.

The present inventor has earnestly investigated and consequently found that obesity can be improved based on the body fat decomposition promoting effect of lactononadecapeptide (LNDP).

The present inventor has further found improvement in pollakiuria based on the urine collection promoting effect, the autonomic nervous activity regulating effect, and the like of LNDP and completed the present invention.

The gist of the present invention is as follows.

[1] A pollakiuria improving agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[2] A urine collection promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[3] An anti-obesity agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[4] A body fat hydrolyzing promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[5] An autonomic nerve activity regulator, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[6] A sympathetic nerve activity promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[7] A white adipose tissue sympathetic nerve activity promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[8] A promoter of the efferent white adipose tissue sympathetic nerve activity, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[9] An adrenal sympathetic nerve activity promoter, comprising: Asn-Ile-Pro-Pro-Leu-Thr-Gln-Thr-Pro-Val- Val-Val-Pro-Pro-Phe-Leu-Gln-Pro-Glu (SEQ ID NO: 1) or a salt thereof as an active ingredient.

[10] A promoter of the efferent adrenal sympathetic nerve activity, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[11] A hypogastric nerve activity promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[12] A promoter of the efferent hypogastric nerve activity, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[13] A parasympathetic nerve activity inhibitor, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[14] A pelvic splanchnic nerve activity inhibitor, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[15] A inhibitor of the efferent pelvic splanchnic nerve activity, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[16] An appetite inhibitor, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[17] An antidiarrheal agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[18] An irritable bowel syndrome improving agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[19] A glycogen hydrolyzing to glucose promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[20] A fatigue recovering agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[21] A cardiotonic agent, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[22] A bronchodilator, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[23] An adrenaline and/or noradrenaline secretion promoter, comprising: Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof as an active ingredient.

[24] Untherapeutic use of Asn-Ile-Pro-Pro-Leu-Thr-Gln-Thr-Pro-Val-Val-Val-Pro-Pro-Phe-Leu-Gln-Pro-Glu or (SEQ ID NO: 1) a salt thereof for improving pollakiuria.

[25] Untherapeutic use of Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof for promoting urine collection.

[26] Untherapeutic use of Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof for anti-obesity.

[27] Use of Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof for preparing a composition for improving pollakiuria.

[28] Use of Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof for preparing a composition for promoting urine collection.

[29] Use of Asn-Ile-Pro-Pro-Leu-Thr-Gln-Thr-Pro-Val-Val-Val-Pro-Pro-Phe-Leu-Gln-Pro-Glu (SEQ ID NO: 1) or a salt thereof for preparing a composition for anti-obesity.

[30] The use according to any one of to, wherein the composition is a food composition or a pharmaceutical composition.

Advantageous Effects of Invention

According to the present invention, new technology relating to anti-obesity can be provided.

DESCRIPTION OF EMBODIMENTS

Figure 1:
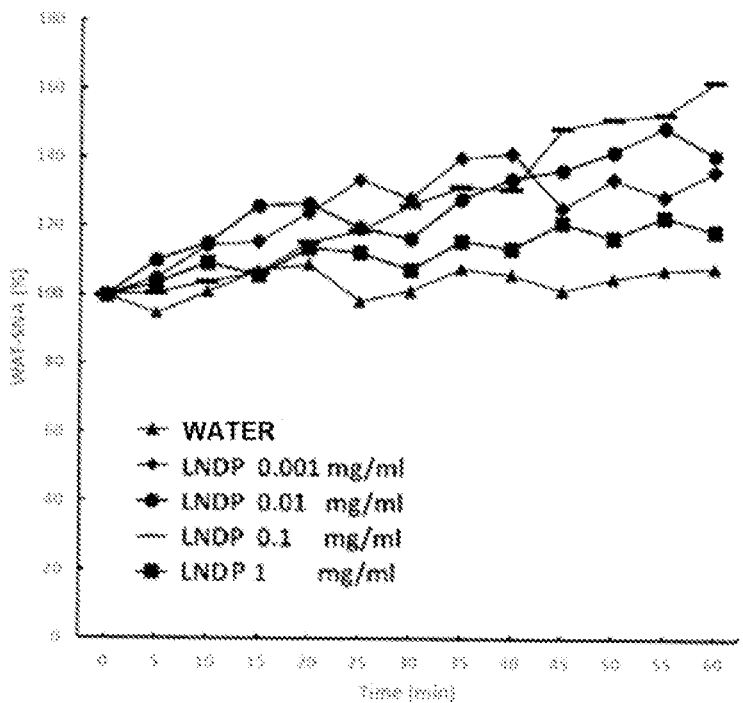
FIG. 1 is a graph relating to changes in the efferent white adipose tissue sympathetic nerve activity (WAT-SNA) when 1 mL/300 g body weight of aqueous solutions containing 0.001, 0.01, 0.1, and 1 mg/mL LNDP, and water were intragastrically administered to rats, respectively.

Although one embodiment of the present invention will be described in detail hereinafter, the present invention is not limited to this.

The present embodiment relates to an anti-obesity agent, and contains lactononadecapeptide (LNDP) or a salt thereof as an active ingredient. Anti-obesity herein means that obesity can be prevented or improved (excessive accumulation of fat is solved or relieved).

LNDP has the sequence Asn-Ile-Pro-Pro-Leu-Thr-Gln-Thr-Pro-Val-Val-Val-Pro-Pro-Phe-Leu-Gln-Pro-Glu represented by the 3-letter code (NIPPLTQTPVVVPPFLQPE represented by the 1-letter code, SEQ ID NO: 1). As to the present invention, the 3-letter code representations and the 1-letter code representations of amino acids, and the representations of peptides follow the general rule well-known to those skilled in the art.

LNDP may be organochemically synthesized, or may be derived from natural substances.

When LNDP is synthesized, the synthesis method is not particularly limited. A common method such as a solid phase method (the t-Boc method or the Fmoc method) or a liquid phase method can be used. LNDP may be synthesized using a peptide automatic synthesizer such as a peptide synthesizer (PSSM-8) described in International Publication No. WO 2011/080947 and manufactured by SHIMADZU CORPORATION. The reaction conditions at the time of synthesis or the method for purifying the obtained peptide is not particularly limited, and those skilled in the art can set the reaction conditions and the purification method suitably.

LNDP is derived from a natural substance, and a method in which LNDP is generated from the natural substance is not particularly limited, either. Examples thereof include a method for fermenting animal milk or milk protein to generate LNDP described in Japanese Patent Laid-Open No. 2013-005757 and a method for subjecting milk casein to enzymatic treatment to generate LNDP described in Japanese Patent Laid-Open No. 2013-005763 and Japanese Patent Laid-Open No. 2015-154773.

The anti-obesity agent of the present embodiment may contain a salt of LNDP instead of LNDP or with LNDP. As such a salt, a salt such as a sodium salt, a potassium salt, or a hydrochloride which can exist under the physiological conditions can be illustrated.

The anti-obesity agent of the present embodiment may contain other components besides LNDP or a salt thereof as long as an object of the present invention can be achieved. In other words, the anti-obesity agent of the present embodiment may be a composition for preventing or improving obesity. For example, the anti-obesity agent of the present embodiment may be a fermented product itself obtained by fermenting animal milk or milk protein or a treated material itself obtained by subjecting animal milk or milk protein to enzymatic treatment.

The form (dosage form) of the anti-obesity agent of the present embodiment is not particularly limited, and the anti-obesity agent can be produced, for example, as a composition for a drug, a quasi drug, or food and drink for humans (especially for humans having obesity symptoms).

When the anti-obesity agent of the present embodiment is prepared as a drug, a quasi drug, or food and drink, for example, an excipient, a binder, a stabilizer, a disintegrator, a lubricant, a corrective, a suspending agent, a coating agent, and other optional components can be mixed with LNDP or a salt thereof for formulation. As dosage forms, tablets, pills, capsules, granules, powder medicine, powder, syrups, and the like are possible, and it is desirable to orally administer these.

Alternatively, although the anti-obesity agent of the present embodiment is not particularly limited, the anti-obesity agent may be food for special uses; food for specified health use, functional nutritional food, or food with function claims, which is health functional food; or the like besides ordinary food and drink when the anti-obesity agent of the present embodiment is produced in an aspect as food and drink. Specific examples of food and drink include supplements, milk, processed milk, milk beverages, soft drinks, alcoholic beverages, fermented food and drink, fermented milk, yogurt, cheese, bread, biscuits, crackers, pizza crust, ice cream, candies, gummi candies, gum, chocolate, modified milk powder, liquid food, food for invalids, food such as milk powder for infants, food such as milk powder for nursing women, freeze-dried food, seasonings, sauces, and noodles.

The anti-obesity agent of the present embodiment may be an aspect such as a drug, feed, or the like for animals other than humans (especially for animals having obesity symptoms) without being limited to a drug, a quasi drug, and food and drink for humans. Examples of the animals other than humans include higher vertebrates other than humans, especially mammals other than humans, and pets such as dogs and cats and domestic animals such as bovines, horses, pigs, sheep can be more specifically illustrated. Additionally, examples thereof include birds, and pet birds such as parakeets and parrots and domestic fowls such as chickens, quails, and turkeys can be more specifically illustrated.

The daily intake of the anti-obesity agent of the present embodiment is not particularly limited, either. For example, in the case of an adult, the content and the like may be adjusted so that LNDP or a salt thereof can be ingested in an amount of 0.001 mg to 1 g, preferably 0.01 mg to 100 mg, more preferably 0.1 mg to 10 mg, further more preferably 1 mg to 5 mg (in terms of the total amount of LNDP and the salt thereof if both LNDP and the salt thereof are contained). The content ratio of LNDP or the salt thereof in the anti-obesity agent of the present embodiment is not particularly limited, either, and may be adjusted depending on the ease of production, a preferable daily dose, and the like.

The number of times of the ingestion of the anti-obesity agent of the present embodiment per day is not particularly limited, either, and can be once or a plurality of times per day, preferably 1 to 3 times/day, and more preferably 1 time/day or 2 times/day.

As mentioned above, new technology relating to anti-obesity can be provided according to the present embodiment.

More specifically, although there are differences among individuals, for example, the decomposition of fat in white adipose tissue can be promoted in a human or a nonhuman animal which has ingested LNDP or the salt thereof according to the present embodiment, for example, by ingesting LNDP or the salt thereof in an aspect such as the above-mentioned drug, quasi drug, or food and drink containing LNDP or the salt thereof (therefore, the present invention also relates to a body fat decomposition promotor containing LNDP which can have the same composition and form (dosage form) as the anti-obesity agent). Consequently, since LNDP or the salt thereof enables promoting the decomposition of fat which has already accumulated in the body and controlling fat accumulation in the body, LNDP or the salt thereof, for example, enables preventing or improving obesity, and can be expected to contribute to improvement in the quality of life (QOL).

Other Embodiments

Although the anti-obesity agent according to the present invention was described above, the present invention can also be used as other embodiments. The present invention may be specifically a pollakiuria improving agent, a urine collection promoter, an autonomic nerve activity regulator, a sympathetic nerve activity promoter, a white adipose tissue sympathetic nerve activity promoter, the promoter of the efferent white adipose tissue sympathetic nerve activity, an adrenal sympathetic nerve activity promoter, the promoter of the efferent adrenal sympathetic nerve activity, a hypogastric nerve activity promoter, the promoter of the efferent hypogastric nerve activity, a parasympathetic nerve activity inhibitor, a pelvic splanchnic nerve activity inhibitor, the inhibitor of the efferent pelvic splanchnic nerve activity, an appetite inhibitor, an antidiarrheal agent, an irritable bowel syndrome improving agent, a glycogen hydrolyzing to glucose promoter, a fatigue recovering agent, a cardiotonic agent, a bronchodilator, or an adrenaline and/or noradrenaline secretion promoter containing LNDP or the salt thereof as an active ingredient.

As to the above-mentioned other embodiments, the composition and the form (dosage form) thereof can be, for example, the same as those of the above-mentioned anti-obesity agent. The description of this point will be omitted.

Pollakiuria improvement mentioned herein means that the frequency of urination can be reduced. Urine collection means collecting urine in the bladder.

LNDP has the effect of enhancing the efferent white adipose tissue sympathetic nerve activity, which is autonomic nerve, and is sympathetic nerve, as understood from Test Example 1. It is known that when the efferent white adipose tissue sympathetic nerve activity is enhanced, the activity of hormone sensitivity lipase of white adipose tissue is enhanced, and lipolysis is promoted, (Timothy J. Bartness, Shrestha, Y. B., Vaughan, C. H., Schwartz, G. J., and Song, C. K., Mol Cell Endocrinol. 2010, 29; 318 (1-2): 34-43. doi: 10.1016/j.mce.2009.08.031. Sensory and sympathetic nerve system control of white adipose tissue lipolysis). Actually, LNDP promotes the hydrolysis of neutral fat, and increases plasma free fatty acid in the same way as in Test Example 5.

Here, the white adipose tissue sympathetic nerve is a sympathetic nerve derived from the T5 to L3 segments of the spinal cord according to Ngoc Ly T. Nguyen, Jessica Randall, Bruce W. Banfield, and Timothy J. Bartness, Am J Physiol Regul Integr Comp Physiol 306: R375-R386, 2014. doi: 10.1152/ajpregu. 00552.2013. Central sympathetic innervations to visceral and subcutaneous white adipose tissue.

According to FIG. 13.3 on P. 308 of Ganong's Review of Medical Physiology 25th edition, 2017, since sympathetic nerves derived from the T5 to L3 segments widely dominate a region from the thorax to the abdomen such as the heart, the lungs, the stomach, the liver, the pancreas, the spleen, the adrenal medulla, the small intestine, the large intestine, the kidneys, the bladder, and the genitals, LNDP also enables regulating the functions of these internal organs based on its effect of regulating the white adipose tissue sympathetic nerve activity. Actually, LNDP promotes the efferent hypogastric nerve activity, which is sympathetic nerve, in the same way as in Test Example 2, and promotes the efferent adrenal sympathetic nerve activity in the same way as in Test Example 4.

Consequently, as to the heart, its activity is enhanced, and the heart copes with an increase in blood volume required at the time of exercise, activities, and excitement. Similarly, as to the lungs, bronchi are expanded, and the lungs cope with an increase in oxygen intake required at the time of exercise, activities, and excitement. As to the liver, glycogen is hydrolyzed to glucose, the release of glucose required at the time of exercise, activities, and excitement to blood is increased. As to the pancreas, insulin secretion is inhibited, and the glucose concentration in blood is increased.

As to the adrenal medulla, the release of adrenaline and a noradrenaline to blood is increased, the sympathetic nerve activity of the whole body is enhanced, the glucose concentration in blood is increased as mentioned above, and exercise, activities, and excitement are induced and maintained thereby.

As to the stomach, appetite can be suppressed by inhibiting its motility.

As to the small intestine, appetite can be first suppressed by controlling its motility. Diarrhea can be suppressed due to a decrease in motility.

Also, as to the large intestine, diarrhea can be suppressed by inhibiting its motility.

These effects on the small intestine and the large intestine can be regulated in the condition of disease such as the irritable bowel syndrome.

As to the bladder, pollakiuria is improved by promoting the efferent hypogastric nerve activity and promoting urine collection as mention below. That is, since more urine can be collected in the bladder, the frequency of urination can be further reduced.

As the genitals, since the ejaculation induction effect is described in CHAPTER 23 "Function of the Male Reproductive System" (p. 501 to 513) of Ganong's Review of Medical Physiology 25th edition, 2017, LNDP can be utilized for infertility treatment or the like. Since the promotion of sexual excitement, vaginal mucus secretion, and vaginal wall contraction is described in CHAPTER 22 "Reproductive Development & Function of the Female Reproductive System" (p. 467 to 499) of Ganong's Review of Medical Physiology 25th edition, 2017, LNDP can be utilized for improvement in frigidity or the like.

Meanwhile, LNDP has the effect of controlling the efferent the pelvic splanchnic nerve activity, which is autonomic nerve, and is parasympathetic nerve, in the same way as in Test Example 3.

The pelvic splanchnic nerve is connected with parasympathetic nerve derived from the S2 to S4 segments of the spinal cord according to FIG. 1 on P. 100 of William C. de Groat, Derek Griffiths, and Naoki Yoshimura, Compr Physiol. 2015 January; 5 (1): 327-396. doi: 10.1002/cphy.c130056, Neural Control of the Lower Urinary Tract. According to FIG. 13.3 on P. 308 of Ganong's Review of Medical Physiology 25th edition, 2017, since the parasympathetic nerves derived from the S2 to S4 segments dominate the large intestine and the genitals simultaneously besides the bladder, LNDP enables adjusting the functions of these internal organs based on its effect of regulating pelvic splanchnic nerve activity.

As to the large intestine, diarrhea can be inhibited by controlling its motility.

This effect enables regulation in the condition of disease such as the irritable bowel syndrome.

As to the genitals, the sexual desire (especially excessive sexual desire) of both men and women can be suppressed as described in CHAPTER 22 "Reproductive Development & Function of the Female Reproductive System" and CHAPTER 23 "Function of the Male Reproductive System" (p. 467 to 513) of Ganong's Review of Medical Physiology 25th edition, 2017.

Therefore, LNDP or the salt thereof can be used for regulating autonomic nerve activity. LNDP or the salt thereof can be used, for example, for the promotion of sympathetic nerve activity, more specifically for the promotion of white adipose tissue sympathetic nerve activity (especially the promotion of the efferent white adipose tissue sympathetic nerve activity), the promotion of adrenal sympathetic nerve activity (especially the promotion of the efferent adrenal sympathetic nerve activity), and the promotion of hypogastric nerve activity (especially the promotion of the efferent hypogastric nerve activity). LNDP or the salt thereof can be used, for example, for the inhibition of parasympathetic nerve activity, more specifically for the inhibition of pelvic splanchnic nerve activity (especially the inhibition of the efferent pelvic splanchnic nerve activity).

LNDP or the salt thereof can be used for improvement in pollakiuria, the promotion of urine collection, the suppression of appetite, antidiarrheal, improvement in the irritable bowel syndrome, the hydrolysis of glycogen to glucose, recovery from fatigue, cardiotonics, bronchiectasis, the promotion of adrenaline secretion, the promotion of noradrenaline secretion, the infertility treatment of males (including human males (men)), ejaculation induction, improvement in female frigidity, vagina contraction, the promotion of vaginal mucus secretion, and the suppression of sexual desire (especially excessive sexual desire).

EXAMPLES

Although the present invention will be described in more detail hereinafter by the Examples, the present invention is not limited to these.

As to LNDP (SEQ ID NO: 1 of the sequence table) used in the Test Examples, LNDP obtained by a solid phase synthesis method (the Fmoc method) was used in all the Test Examples.

Test Example 1 Effect of Enhancing White Adipose Tissue Sympathetic Nervous Activity If the efferent white adipose tissue sympathetic nerve activity is enhanced, the hormone sensitive lipase activity of white adipose tissue is enhanced, the hydrolysis of neutral fat stored in white adipose cells is promoted, and the produced glycerol and fatty acid is released to blood and utilized as energy. Therefore, LNDP's effect of enhancing the white adipose tissue sympathetic nerve activity was tested using rats. Here, an efferent nerve refers to transmit command of the central nerve system to tissue.

Male Wistar rats with a weight of around 300 g raised for 1 week or more at a thermostat animal room at 24° C. in a cycle including a 12-hour light period and a 12-hour dark period (the lamp is lit from 8:00 to 20:00) were used. Each rat was urethane-anesthetized after a 3-hour fast on the day of the test, and a cannula for intragastric administration was inserted. Then, the abdomen was opened, an epididymal white adipose tissue sympathetic nerve was lifted with silver electrodes, and its electric activity was measured. When the measured value of this nervous activity stabilized, 1 mL/300 g body weight of a solution containing LNDP was intragastrically administered using the cannula. A change in this nerve activity was measured for 60 minutes. As a control experiment, a change in the white adipose tissue sympathetic nerve activity when 1 mL/300 g body weight of water was intragastrically administered was measured. The data of these nerve activities were analyzed by the average value of the firing rate per 5 seconds (pulse/5 s) of every 5 minutes and expressed in terms of the percentage with the average value for 5 minutes before the stimulation start (value at 0 minutes) defined as 100%. The average value±the standard error was calculated from the data, and the statistically significant difference as groups was subjected to a statistical test by the analysis of variance (ANOVA) with repeated measures. The statistically significant difference between the absolute values of the nerve activities before the oral intragastric administration start (0 minutes) was subjected to a statistical test by the Mann-Whitney U-test.

First, each one rat was tested using each LNDP solution ranging from 0.001 mg/1 mb/300 g body weight to 1 mg/1 mL/300 g body weight to grasp dose dependency roughly (FIG. 1). As the white adipose tissue sympathetic nerve activity (WAT-SNA) before the intragastric administration (0 minutes) is defined as 100% in terms of the percentage, when 1 mL/300 g body weight of water was intragastrically administered as a control, the WAT-SNA hardly changed; the WAT-SNA value gave a minimum value of 94.7% 5 minutes after the administration, a maximum value of 108.9% 20 minutes after the administration, and a value between these values during the measurement period other than the above time points. Meanwhile, when 1 mL/300 g body weight of an aqueous LNDP solution of 0.001 mg/mL was intragastrically administered, the WAT-SNA increased gradually, gave a maximum value of 141.3% 40 minutes after the administration, then decreased slightly, and however gave 136.2% 60 minutes after the administration. Similarly, when a 0.01 mg/mL solution was administered, the WAT-SNA gave a maximum value of 149.1% 55 minutes later. When a 0.1 mg/mL solution was administered, the WAT-SNA gave a maximum value of 162.4% 60 minutes later. When a 1 mg/mL solution was administered, the WAT-SNA gave a maximum value of 123. % 55 minutes later.

Figure 2:
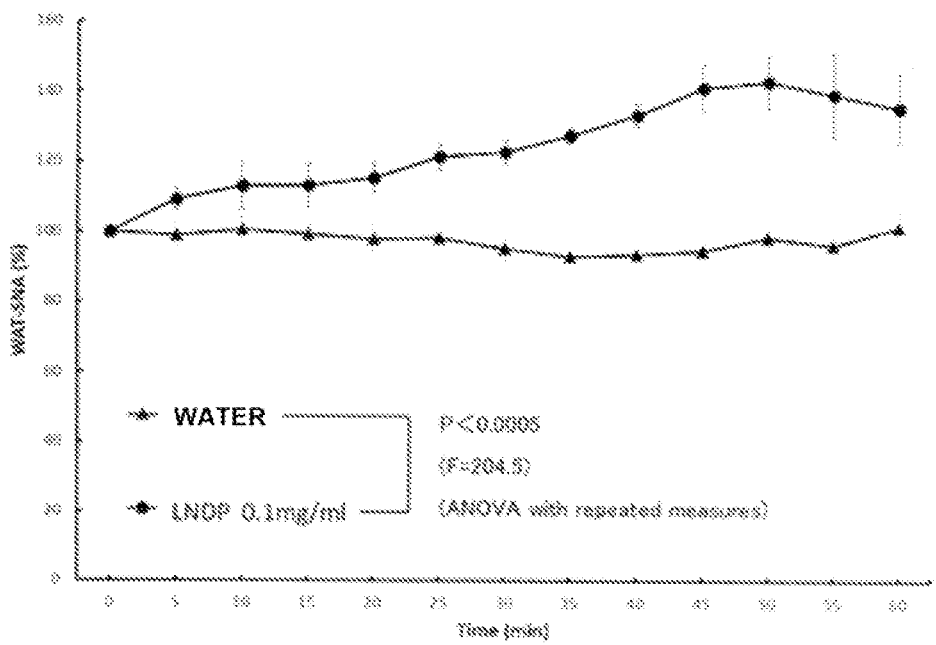
FIG. 2 is a graph relating to changes in the efferent white adipose tissue sympathetic nerve activity (WAT-SNA) when 1 mL/300 g body weight of an aqueous solution containing 0.1 mg/mL LNDP and water were intragastrically administered to rats, respectively.

Next, three rats were tested in each group to confirm the effect statistically (FIG. 2). When 1 mL/300 g body weight of water was intragastrically administered as a control, the WAT-SNA hardly changed; it gave a minimum value of 93.2±1.3% 35 minutes after the administration, a maximum value of 101.9±4.4% 60 minutes after the administration, and a value between these values during the measurement period other than the above time points. Meanwhile, when 1 mL/300 g body weight of an aqueous solution containing 0.1 mg/mL LNDP was intragastrically administered, the WAT- SNA increased gradually, gave a maximum value of 143.2±7.7% 50 minutes after the administration, and then stopped at a value near that.

A significant difference by the Mann-Whitney U-test was not observed between the absolute values of the WAT-SNAs of these two groups directly before the administration (0 minutes). When the WAT-SNA values of these two groups from 5 minutes to 60 minutes after the intragastric administration were analyzed as groups by the ANOVA with repeated measures, a significant difference was observed between the WAT-SNA values at the time of water administration performed as a control and at the time of LNDP administration ($P<0.0005$, $F=204.5$ by ANOVA with repeated measures).

It was confirmed from the above that LNDP had the capability to enhance the efferent white adipose tissue sympathetic nerve activity, which promote the hydrolysis of neutral fat stored in white adipose cells, by the oral intragastric administration.

As mentioned above, the white adipose tissue sympathetic nerve is a sympathetic nerve derived from the T5 to L3 segments of the spinal cord, the sympathetic nerves derived from the T5 to L3 segments widely dominate a region from the thorax to the abdomen such as the heart, the lungs, the stomach, the liver, the pancreas, the spleen, the adrenal medulla, the small intestine, the large intestine, the kidneys, the bladder, and the genitals, and therefore LNDP also enables regulating the functions of these internal organs based on its effect of regulating the white adipose tissue sympathetic nerve activity. Actually, LNDP promotes the efferent hypogastric nerve activity, which is a sympathetic nerve, in the same way as Test Example 2 and the efferent adrenal sympathetic nerve activity in the same way as in Test Example 4.

Test Example 2 Effect of Enhancing Hypogastric Nerve Activity

Test Example 1 showed that LNDP regulated the activity of sympathetic nerves derived from the T5 to L3 segments of the spinal cord. It is known that hypogastric nerve, which is a sympathetic nerve derived from the T11 to L2 segments among the T5 to L3 segments of the spinal cord, dominates internal organs and tissues such as the bladder, the small intestine, the large intestine, and the genitals of the abdomen. Since it is known that the promotion of the efferent the hypogastric nerve activity (HGNA) enables relaxing the detrusor muscle, contracting the internal urethral sphincter, inhibiting urination which occurs involuntarily and collecting urine, an effect which the intragastric administration of LNDP has on the HGNA was examined.

Male Wistar rats with a weight of around 300 g raised in a thermostat animal room at 24° C. in a cycle including a 12-hour light period and a 12-hour dark period for 1 week or more were used. Each rat was urethane-anesthetized after a 3-hour fast on the day of the test, and a cannula for intragastric administration was inserted. Then, the abdomen was opened, the efferent hypogastric nerve was lifted with silver electrodes, and its electric activity was measured. When the measured value stabilized, 1 mL/300 g body weight of an aqueous solution containing LNDP was intragastrically administered using the cannula. A change in the efferent hypogastric nerve activity was electrophysiologically measured for 60 minutes. As a control experiment, a change in the efferent hypogastric nerve activity when 1 mL/300 g body weight of water was intragastrically administered was measured. A tube is inserted in the trachea to secure the respiratory tract, and the body temperature (rat rectal temperature) was maintained at 37.0±0.5° C. with a warmer from the operation start to the measurement end. The data of these nerve activities were analyzed by the average value of the firing rate per 5 seconds (pulse/5 s) of every 5 minutes and expressed in terms of the percentage with the average value for 5 minutes before the stimulation start (value at 0 minutes) defined as 100%. The average value±the standard error was calculated from the data, and the statistically significant difference as groups was subjected to a statistical test by the ANOVA with repeated measures. The statistically significant difference between the absolute values of the nerve activities before the oral intragastric administration start (0 minutes) was subjected to a statistical test by the Mann-Whitney U-test.

Figure 3:
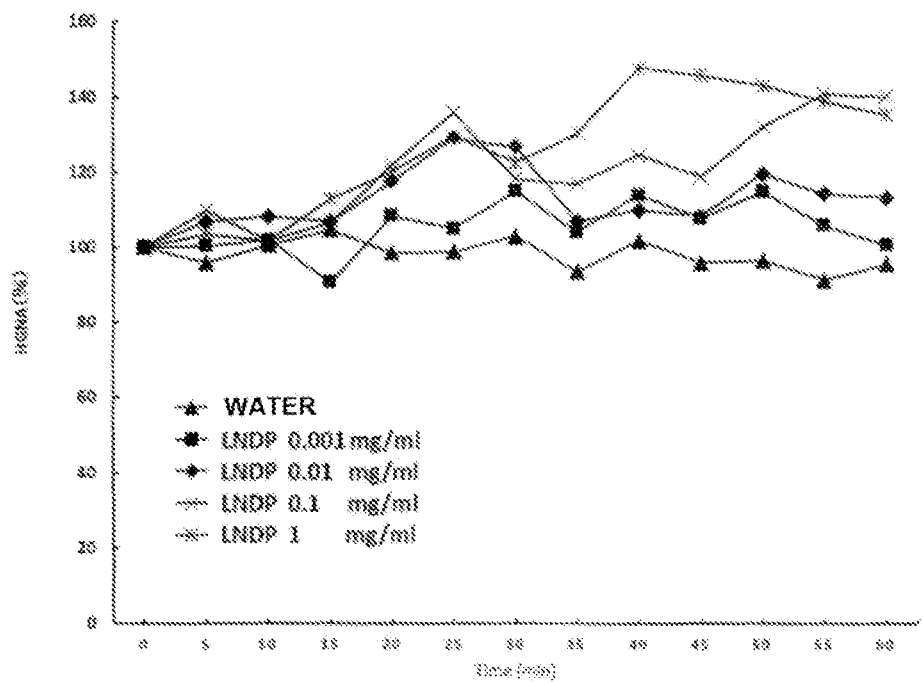
FIG. 3 is a graph relating to changes in the efferent hypogastric nerve activity (HGNA) when 1 mL/300 g body weight of aqueous solutions containing 0.001, 0.01, 0.1, and 1 mg/mL LNDP, and water were intragastrically administered to rats, respectively.

First, a test was performed by administering each LNDP solution ranging from 0.001 mg/mL/300 g body weight to 1 mg/mL/300 g body weight to each one rat to grasp dose dependency roughly (FIG. 3). When 1 mL/300 g body weight of water was intragastrically administered as a control experiment, the HGNA hardly changed; the HGNA value gave a maximum value of 104.7% 15 minutes after the administration, a minimum value of 91.6% 55 minutes after the administration, and a value between those values during the measurement period other than the above time points. Meanwhile, when 1 mL/300 g body weight of a 0.001 mg/mL LNDP was intragastrically administered, the HGNA decreased slightly at first, decreased further to a minimum value of 90.8% 15 minutes after the administration, then, however, increased to a maximum value of 115.1% 50 minutes after the administration, and then decreased. When 1 mL/300 g body weight of 0.01 mg/mL LNDP was intragastrically administered, the HGNA increased slightly, gave a maximum value of 129.2% 25 minutes after the administration, then decreased slightly, and, however, gave 113.5% 60 minutes after the administration. When 1 mL/300 g body weight of 0.1 mg/mL LNDP was intragastrically administered, the HGNA increased gradually, and gave a maximum value of 141.1% 55 minutes after the administration. When 1 mL/300 g body weight of 1 mg/mL LNDP was intragastrically administered, the HGNA increased, gave a maximum value of 147.8% 40 minutes after the administration, and then remained at values near that.

Figure 4:
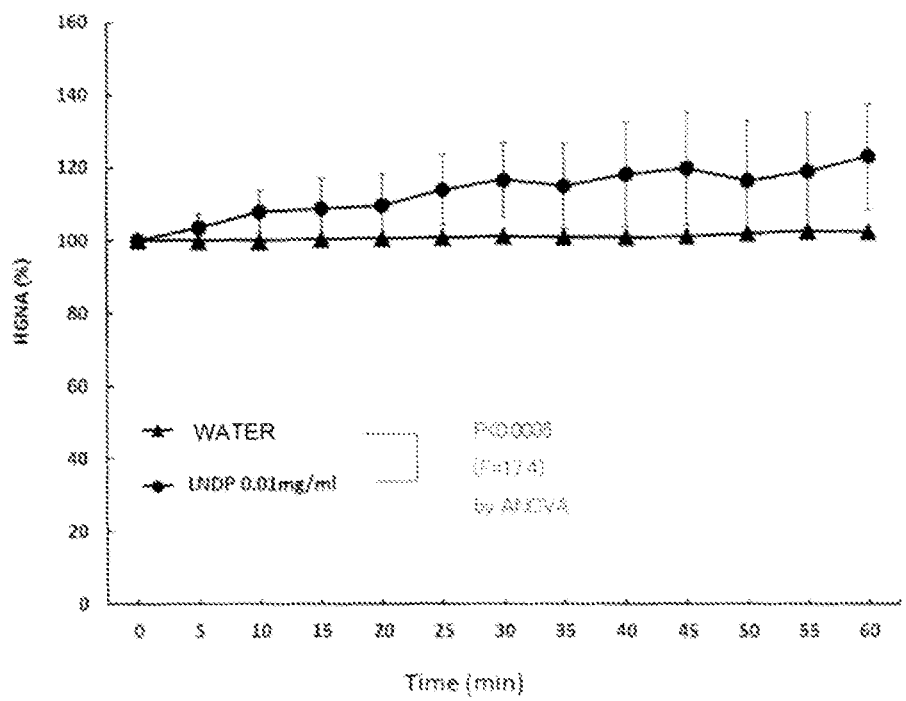
FIG. 4 is a graph relating to changes in the efferent hypogastric nerve activity (HGNA) when 1 mL/300 g body weight of an aqueous solution containing 0.01 mg/mL LNDP and water were intragastrically administered to rats, respectively.

Next, three rats each were tested to confirm the effect statistically. When 1 mL/300 g body weight of water was intragastrically administered as a control experiment, the HGNA hardly changed: the HGNA value gave a minimum value of 99.95±0.41% 10 minutes after the administration, a maximum value of 102.6±0.9% 55 minutes later, and remained at values between these during the measurement period other than the above time points. Meanwhile, when 1 mL/300 g body weight of an aqueous solution containing 0.01 mg/mL LNDP was intragastrically administered, the HGNA increased gradually, and gave a maximum value of 123.1±14.6% 60 minutes after the administration (FIG. 4).

A significant difference by the Mann-Whitney U-test was not observed between the HGNAs of these two groups directly before the intragastric administration (0 minutes). When the statistical analysis was performed by the ANOVA with repeated measures which analyzes the HGNA values of these two groups from 5 minutes to 60 minutes after the intragastric administration as groups, a significant difference was observed between the HGNA values of the water treatment group and the 0.01 mg/mL LNDP treatment group ($P<0.0005$, $F=17.4$ by ANOVA with repeated measures).

Figure 5:
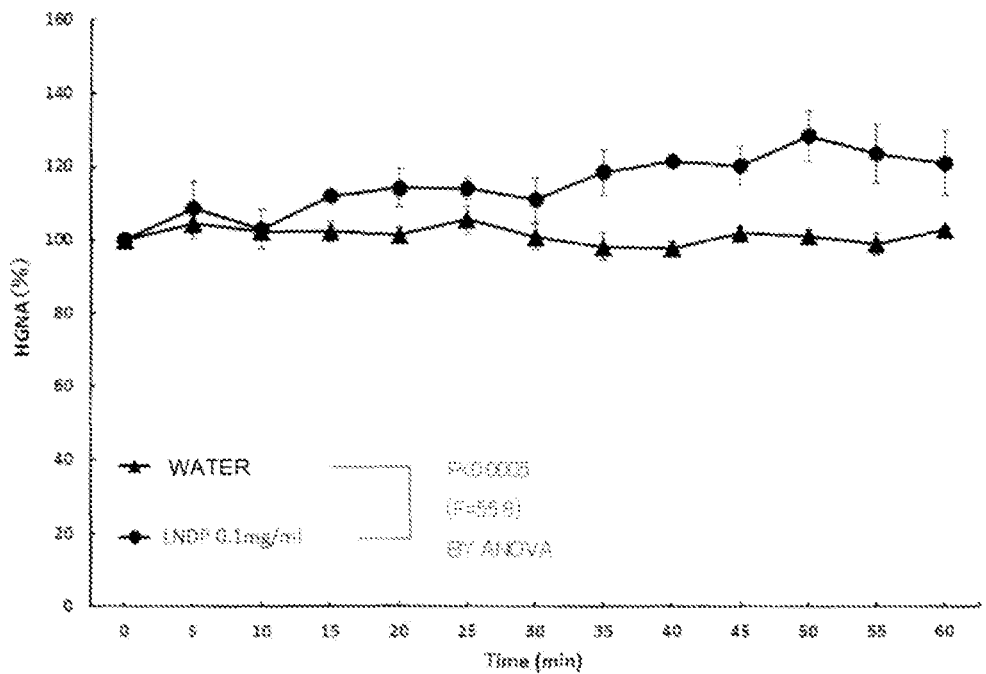
FIG. 5 is a graph relating to changes in the efferent hypogastric nerve activity (HGNA) when 1 mL/300 g body weight of an aqueous solution containing 0.1 mg/mL LNDP and water were intragastrically administered to rats, respectively.

Furthermore, when 1 mL/300 g body weight of an aqueous solution containing 0.1 mg/mL of LNDP was intragastrically administered, the HGNA increased gradually, gave a maximum value of 128.5±6.9% 50 minutes after the intragastric administration, and then remained at values near that. Meanwhile, when 1 mL/300 g body weight of water was intragastrically administered, the HGNA hardly changed; the HGNA value gave a maximum value of 105.5±3.8% 25 minutes after the intragastric administration, a minimum value of 97.9±1.6% 40 minutes later, and remained at values between these values during the measurement period other than the above time points (FIG. 5).

A significant difference by the Mann-Whitney U-test was not observed between the HGNAs of these two groups directly before the intragastric administration (0 minutes). When the statistical analysis was performed by the ANOVA with repeated measures which analyzes the HGNA values of these two groups from 5 minutes to 60 minutes after the intragastric administration as groups, a significant difference was observed between the HGNA values of the water treatment group and the 0.1 mg/mL LNDP treatment group ($P<0.0005$, $F=55.8$ by ANOVA with repeated measures).

It was confirmed from the above that LNDP enhances the efferent hypogastric nerve activity derived from the T11 to L2 segments of the spinal cord by oral administration. Therefore, LNDP has a capability to inhibit urination and reduce the frequency of urination.

Test Example 3 Effect of Controlling Pelvic Splanchnic Nerve Activity

It is known that when the efferent pelvic splanchnic nerve activity, which is parasympathetic nerve, (PSNA) is promoted, the detrusor muscle of the bladder is contracted, and when the PSNA is inhibited, the detrusor muscle is relaxed. Therefore, the effect of the intragastric administration of LNDP on the PSNA was examined. As to the efferent pelvic splanchnic nerve, pelvic splanchnic nerve is a parasympathetic nerve which is derived from the S2 to S4 segments of the spinal cord and dominate internal organs and tissues such as the bladder, the large intestine, and the genitals of the abdomen, and an efferent nerve refers to transmit command of the central nerve system to tissue.

Male Wistar rats with a weight of around 300 g raised in a thermostat animal room at 24° C. in a cycle including a 12-hour light period and a 12-hour dark period for 1 week or more were used. Each rat was urethane-anesthetized after a 3-hour fast on the day of the test, and a cannula for intragastric administration was inserted. Then, the abdomen was opened, an efferent pelvic splanchnic nerve was lifted with silver electrodes, and its electric activity was measured. When this measured value stabilized, 1 mL/300 g body weight of an aqueous solution containing 0.1 mg/mL LNDP was intragastrically administered using the cannula. A change in the efferent pelvic splanchnic nerve activity was electrophysiologically measured using three rats each for 60 minutes. As a control experiment, a change in the activity of the pelvic splanchnic nerves when 1 mL/300 g body weight of water was intragastrically administered was measured. A tube is inserted in the trachea to secure the respiratory tract, and the body temperature (rat rectal temperature) was maintained at 37.0±0.5° C. with a warmer from the operation start to the measurement end. The data of the pelvic splanchnic nerve activities were analyzed by the average value of the firing rate per 5 seconds (pulse/5 s) of every 5 minutes and expressed in terms of the percentage with the average value for 5 minutes before the stimulation start (value at 0 minutes) defined as 100%. The average value±the standard error was calculated from the data, and the statistically significant difference as groups was subjected to a statistical test by the ANOVA with repeated measures. The statistically significant difference between the absolute values of the nervous activities before the intragastric administration (0 minutes) was subjected to a statistical test by the Mann-Whitney U-test.

Figure 6:
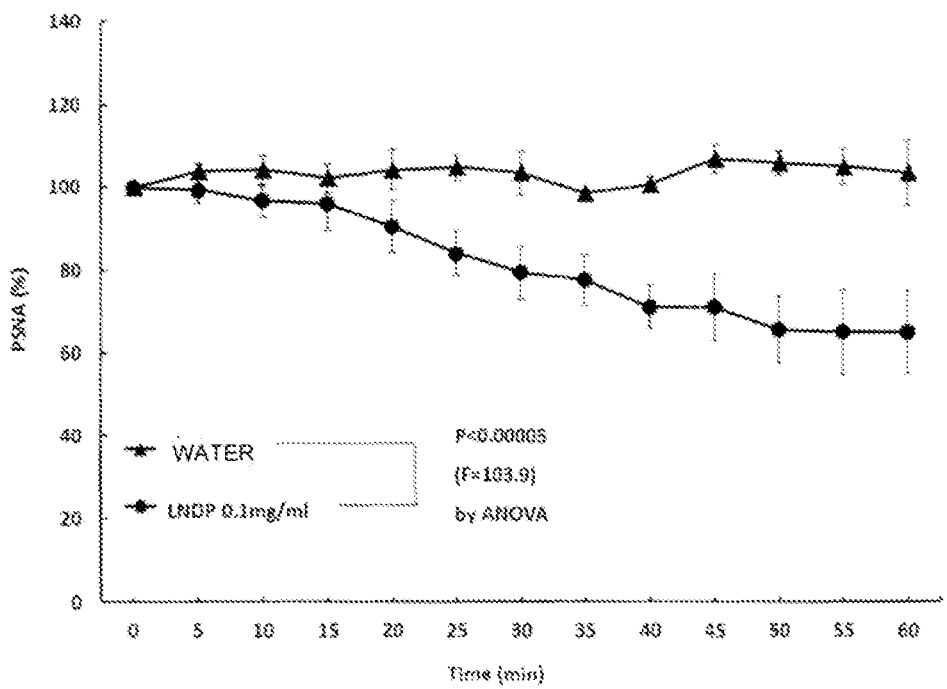
FIG. 6 is a graph relating to changes in the efferent pelvic splanchnic nerve activity (PSNA) when 1 mL/300 g body weight of an aqueous solution containing 0.1 mg/mL LNDP and water were intragastrically administered to rats, respectively.

When 1 mL/300 g body weight of water was intragastrically administered, the PSNA hardly changed; the PSNA value gave a minimum value of 98.6±0.6% 35 minutes after the intragastric administration, a maximum value of 107.0±3.3% 45 minutes later, and remained at values between these values during the measurement period other than the above time points. Meanwhile, when 1 mL/300 g body weight of an aqueous solution containing 0.1 mg/mL of LNDP was intragastrically administered, the PSNA decreased gradually, and gave a minimum value of 65.1±10.0% 60 minutes after the intragastric administration (FIG. 6).

A significant difference was not observed between the absolute values of the PSNAs of these two groups directly before the intragastric administration (0 minutes). A significant difference was observed between the rates of change in the PSNA of the water treatment group and the PSNA of the LNDP treatment group from 5 minutes to 60 minutes after the intragastric administration ($P<0.0005$, $F=103.9$ by ANOVA with repeated measures).

It was confirmed from the above that LNDP controlled the pelvic splanchnic nerve activity by oral administration. Therefore, LNDP has the capability to inhibit urination and reduce the frequency of urination.

Test Example 4 Effect of Enhancing Adrenal Gland Sympathetic Nervous Activity

Test Example 1 showed that LNDP regulates the activity of the sympathetic nerves derived from the T5 to L3 segments of the spinal cord. It is known that the adrenal sympathetic nerve, which is a sympathetic nerve derived from the T9 to T10 segments among the T5 to L3 segments of the spinal cord, dominates the adrenal medulla.

If the adrenal sympathetic nerve activity is enhanced, an increase in the release of adrenaline and noradrenaline from the adrenal medulla to blood enable and an increase in the glucose concentration in blood enable inducing and maintaining exercise, activities, and excitement. Therefore, the effect of LNDP intragastric administration on the efferent adrenal sympathetic nerve activity (ASNA) was examined.

Male Wistar rats with a weight of around 300 g raised in a thermostat animal room at 24° C. in a cycle including a 12-hour light period and a 12-hour dark period for 1 week or more were used. Each rat was urethane-anesthetized after a 3-hour fast on the day of the test, and a cannula for intragastric administration was inserted. Then, the abdomen was opened, the efferent adrenal sympathetic nerve was lifted with silver electrodes, and its electric activity was measured. When this measured value stabilized, 1 mL/300 g body weight of an aqueous solution containing 0.1 mg/mL LNDP was intragastrically administered using the cannula. A change in the adrenal sympathetic nerve activity was electrophysiologically measured for 60 minutes. As a control experiment, a change in the hypogastric nerve activity when 1 mL/300 g body weight of water was intragastrically administered was measured. A tube is inserted in the trachea to secure the respiratory tract, and the body temperature (rat rectal temperature) was maintained at 37.0±0.5° C. with a warmer from the operation start to the measurement end. The data of these nerve activities were analyzed by the average value of the firing rate per 5 seconds (pulse/5 s) of every 5 minutes and expressed in terms of the percentage with the average value for 5 minutes before the stimulation start (value at 0 minutes) defined as 100%. The average value±the standard error was calculated from the data, and the statistically significant difference as groups was subjected to a statistical test by the ANOVA with repeated measures. The statistically significant difference between the absolute values of the nervous activities before the oral intragastric administration start (0 minutes) was subjected to a statistical test by the Mann-Whitney U-test.

Figure 7:
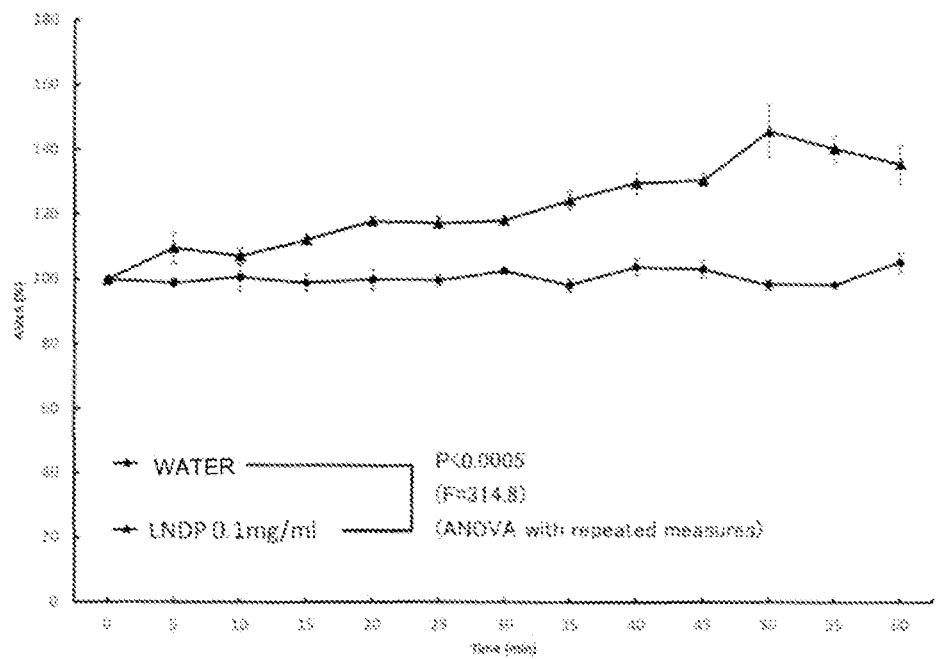
FIG. 7 is a graph relating to changes in the efferent adrenal sympathetic nerve activity (ASNA) when 1 mL/300 g body weight of an aqueous solution containing 0.1 mg/mL LNDP and water were intragastrically administered to rats, respectively.

When 1 mL/300 g body weight of water was intragastrically administered, the ASNA hardly changed; the ASNA value gave a minimum value of 98.1±2.0% 35 minutes after the intragastric administration, a maximum value of 105.2±3.1% 60 minutes later, and remained at values between these values during the measurement period other than the above time points. Meanwhile, when 1 mL/300 g body weight of an aqueous solution containing 0.1 mg/mL of LNDP was intragastrically administered, the ASNA increased gradually, gave a maximum value of 145.9±8.2% 50 minutes after the intragastric administration, and then stopped at values near that (FIG. 7).

A significant difference was not observed between the absolute values of the ASNAs of these two groups directly before the administration (0 minutes). A significant difference was observed between the rates of change in the ASNA of the water treatment group and the ASNA of the LNDP treatment group from 5 minutes to 60 minutes after the intragastric administration (P<0.0005, F=314.8 by ANOVA with repeated measures).

It was confirmed from the above that LNDP promotes the adrenal sympathetic nerve activity by oral administration. Therefore, LNDP has the capability to induce and maintain exercise, activities, and excitement by promoting the release of adrenaline and noradrenaline from the adrenal medulla to blood and increasing the glucose concentration in blood.

Test Example 5 Effect of Hydrolyzing Neutral Fat and Releasing Free Fatty Acid to Blood It was tested whether LNDP's effect of enhancing the efferent white adipose tissue sympathetic nerve activity actually hydrolyzes neutral fat stored in this tissue to release to blood as free fatty acid or not using six rats in each group.

Figure 8:
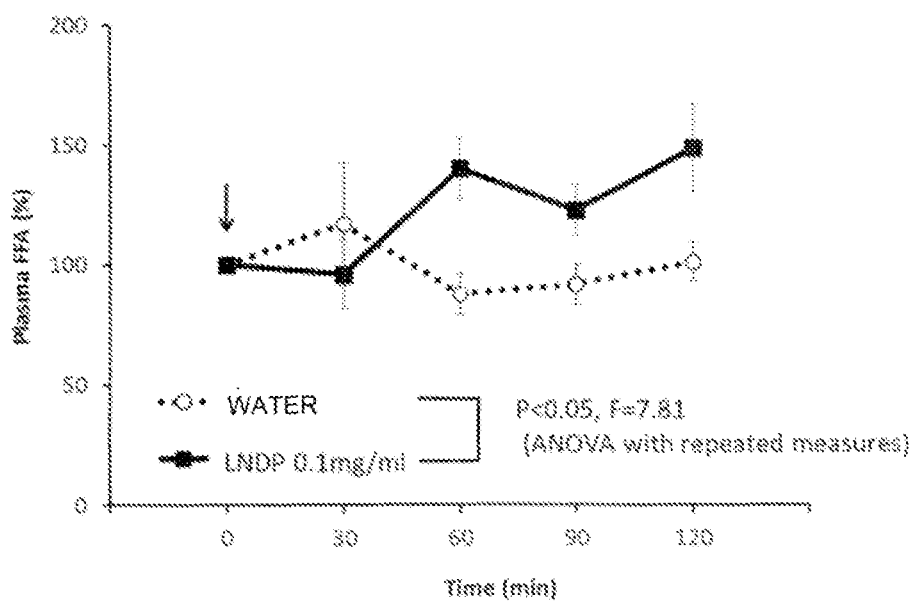
FIG. 8 is a graph relating to changes in the concentration of plasma free fatty acid (plasma FFA) when 1 mL/300 g body weight of an aqueous solution containing 0.1 mg/mL LNDP and water were intragastrically administered to rats, respectively.

Male Wistar rats (around 9 weeks old) with a weight of around 300 g were used which were raised in a thermostat animal room at 24° C. in a cycle including a 12-hour light period and a 12-hour dark period (the lamp is lit from 8:00 to 20:00) for 1 week or more. A cannula for collecting blood was inserted in the right jugular vein under anesthesia using pentobarbital sodium (35 mg/kg, ip) and ketamine hydrochloride (75 mg/kg, ip) 3 days before the experiment. Feed was removed directly before the experiment start on the day, blood was collected using a venous cannula under no anesthesia before administration, 1 mL/300 g body weight of an aqueous solution containing 0.1 mg/mL LNDP, or water was then intragastrically administered using a sonde for intragastric administration, and blood was collected 30 minutes, 60 minutes, 90 minutes, and 120 minutes after the intragastric administration. EDTA (300 nmol/0.01 mL EDTA) was mixed into 0.2 mL of the collected blood sample, and plasma was collected by centrifugality. The plasma free fatty acid concentration (plasma FFA) was immediately measured by an enzyme method (NEFA C-Test Wako L, manufactured by FUJIFILM Wako Pure Chemical Corporation) after the plasma collection. The data were expressed in terms of the percentage with the absolute value of plasma FFA before the intragastric administration of LNDP or water (value at 0 minutes) defined as 100%. The average value±the standard error was calculated from the data, the statistically significant difference as groups was subjected to a statistical test by the analysis of variance (ANOVA) with repeated measures. The statistically significant difference between the absolute values of plasma FFA before the intragastric administration start (0 minutes) was subjected to a statistical test by the Mann-Whitney U-test. FIG. 8 shows the results.

When 1 mL/300 g body weight of water was intragastrically administered as a control, the plasma FFA concentration first increased slightly, gave 117.1±25.7% 30 minutes after the administration, however, then decreased, gave a minimum value of 88.0±8.4% 60 minutes after the administration, then stopped at a little higher values than that, and gave 101.3±8.1% 120 minutes after the administration. Meanwhile, when 1 mL/300 g body weight of an aqueous solution containing 0.1 mg/mL of LNDP was intragastrically administered, the plasma FFA concentration decreased to a minimum value of 96.0±14.3% 30 minutes after the administration, however, then increased, and gave a maximum value of 149.0±18.1% 120 minutes after the administration.

A significant difference by the Mann-Whitney U-test was not observed between the absolute values of the plasma FFA concentrations of the rats in these two groups directly before the intragastric administration (0 minutes). The plasma FFA concentrations of these two groups from 30 minutes to 120 minutes after the intragastric administration were statistically analyzed by the ANOVA with repeated measures. Consequently, a significant difference was observed between the value of the plasma FFA concentration of the water treatment group and the value of the plasma FFA concentration of the LNDP treatment group (water treatment group vs. LNDP treatment group: P<0.05, F=7.81 by the ANOVA with repeated measures). These results made it clear that the intragastric administration of LNDP increased the plasma FFA concentration significantly.

When the efferent white adipose tissue sympathetic nerve is excited, hormone sensitive lipase of white adipose tissue is activated, the accumulated neutral fat is hydrolyzed into fatty acid and glycerin, and the lipolysis is promoted. The result which shows that the intragastric administration of 1 mL/300 g body weight of an aqueous LNDP solution of 0.1 mg/mL significantly promotes the epididymal white adipose tissue sympathetic nerve activity of the urethane-anesthetized rats was obtained in Test Example 1. Therefore, the result made it clear in combination with the result obtained in Test Example 5 that LNDP has the function of exciting sympathetic nerve which dominate the nerve of white adipose tissue and promoting the hydrolysis of neutral fat into fatty acid and glycerin in white adipose tissue. That is, it is considered that LNDP has the anti-obesity effect of hydrolyzing body fat. The dosage at which it was confirmed that the efferent white adipose tissue sympathetic nerve activity was statistically and significantly enhanced, and it was confirmed that neutral fat was hydrolyzed to release free fatty acid to blood at 0.1 mg/mL. However, the efferent white adipose tissue sympathetic nerve activity is increased at 0.001 to 1 mg/mL in Test Example 1, and it is therefore considered that neutral fat is hydrolyzed to release free fatty acid to blood similarly also at 0.001 to 1 mg/mL.

Test Example 6 Effect of Reducing Frequency of Urination/Day and Increasing the Urination Amount/Time in Spontaneous Urination It was confirmed from Test Example 2 that LNDP promotes the efferent hypogastric nerve activity, and it was confirmed from Test Example 3 that LNDP inhibits the efferent the pelvic splanchnic nerve activity. Influence on the bladder, which is one of the internal organs dominated by these nerves, was therefore investigated. It was specifically confirmed by spontaneous urination tests using rats whether LNDP actually reduced the frequency of urination per day by increasing the urination amount per time, and contributes to improvement in pollakiuria.

Male Wistar rats which are 13 weeks old were received, and quarantined and acclimated in a thermostat animal room at 18 to 28° C. in a cycle including a 12-hour light period and a 12-hour dark period for 1 week, and ten 14- to 16-week-old rats per group were tested. An aqueous 0.1 mg/mL LNDP solution or water was ingested from drinking for 7 days, and the urination amount was measured as weight with an electronic balance installed under a urine-collecting opening in raising with a metabolism cage. The weight data of the electronic balance every minute were automatically inputted into a computer. The weight data of the electronic balance were chronologically confirmed as to each individual, an increase in weight was considered as one time of urination, and the difference between the maximum value and the immediately preceding minimum value was defined as one time of the urination amount. The total urination amount and the frequency of urination per day were found, and the urine amount per one time of urination (=the total urination amount per day/the frequency of urination per day) was calculated as to an individual of each group. In a statistical method for comparing two groups, the Student's t-test was performed when the uniformity of the variance was observed by the F-test, the t-test of Aspin-Welch was performed when the uniformity of the variance was not observed, and the rank sum test of Wilcoxson was performed as to the measured values including the frequency of urination. As to the comparison of the test substance and ingestion days with respect to each measured value, two-way analysis of variance (two-way ANOVA) with replication was performed.

Consequently, when the aqueous 0.1 mg/mL LNDP solution ingestion group was compared with the water ingestion group, the significant differences in change in body weight, the general symptoms, the amount of feed ingested per day, the amount of drinking per day, and the urination amount per day were not observed. Meanwhile, the frequency of urination per day of the water ingestion group was 18.6±0.5, the frequency of urination per day of the aqueous LNDP solution ingestion group was 15.8±0.4, and a significant decrease in the frequency of urination was observed in the aqueous LNDP solution ingestion group as compared with the water ingestion group. In the two-way analysis of variance as to the frequency of urination per day, the significant decrease due to aqueous LNDP solution ingestion was observed, and the influence of ingestion days and interaction was not observed. The urination amount per time of the water ingestion group was 1.20±0.03 g, the average value of the urine amount per time of the aqueous LNDP solution ingestion group was 1.41±0.05 g, and a significant increase in the urination amount per time was observed in the aqueous LNDP solution ingestion group as compared with the water ingestion group. In the two-way analysis of variance as to the urination amount per time, a significant increase due to the aqueous LNDP solution ingestion was observed, and the influence due to the ingestion days and interaction was not observed.

Similarly, the average value of the urination amount per time/body weight kg of the water ingestion group was 2.93±0.09 g, and the average value of the urination amount per time/body weight kg of the aqueous LNDP solution ingestion group was 3.44±0.13 g. A significant increase in the urination amount per time/body weight was observed in the aqueous LNDP solution ingestion group as compared with the water ingestion group, and a significant increase due to the aqueous LNDP solution ingestion was observed, and the influences of the ingestion days and interaction were not observed in the two-way analysis of variance (Table 1).

TABLE 1

Influence of LNDP on rat spontaneous urination

| Test group | Frequency of urination (time/day) | | | | Urination amount (g/day) | | | | Urination amount per time (g/time) | | | |
|---|---|---|---|---|---|---|---|---|---|---|---|---|
| | Average | Standard error | % | p value | Average | Standard error | % | p value | Average | Standard error | % | p value |
| Water | 18.6 | 0.5 | 100 | — | 53.09 | 1.53 | 100 | — | 1.20 | 0.03 | 100 | — |
| Aqueous 0.1 mg/ml LNDP solution | 15.8 | 0.4 | 85 | 1) 0.00008 2) 0.0007 | 52.44 | 1.72 | 99 | — | 1.41 | 0.05 | 18 | 1) 0.002 2) 0.009 | p value: water vs LNDP
1) tow-way ANOVA main effect
2) Wilcoxon rank sum test

It was confirmed from the above by the spontaneous urination test that when urine collection was promoted by the ingestion of LNDP, the urination amount per time increased, and the frequency of urination per day decreased, which contributes to improvement in pollakiuria. The dosage of LNDP used for spontaneous urination is 0.1 mg/mL at which the hypogastric nerve activity is statistically and significantly enhanced, and the pelvic splanchnic nerve activity is statistically and significantly controlled. The causal relationship between both was confirmed. Therefore, pollakiuria in spontaneous urination can be improved at 0.01 to 0.1 mg/mL at which it is confirmed that the hypogastric nerve activity is statistically and significantly enhanced.

Test Example 7 Pollakiuria Improving Effect (1)

The influence of LNDP on the frequency of urination was examined by randomized, double-blinded, placebo-controlled, crossover, comparative study on 14 persons which are healthy men and women of ages of 40 or more and less than 65 with slight pollakiuria symptoms. The test was performed using test foods containing LNDP and placebo foods not containing LNDP as test meals. Specifically, the 14 persons were divided into 2 groups each having 7 persons, and, in one group, the persons were made to ingest the test foods for 14 days and ingest placebo foods for 14 days after a 14-day washout period. In the other group, the persons were made to ingest the placebo foods for 14 days and ingest test foods for 14 days after a 14-day washout period. The below-mentioned tablets were used for test meals, and the test meal was ingested in a dosage of 4 tablets after dinner. Since the test foods contain 0.6 mg per tablet of LNDP as mention below, LNDP contained in a dose of test food is 2.4 mg, and the daily LNDP intake of a person belonging to the group which ingests test foods is also 2.4 mg. The subjects were asked to write urination diaries recording the frequencies of urination and the urination times during the test period, and the influence of LNDP on the frequency of urination was evaluated using this.

Tablets comprising a casein enzymolysis product, lactose, maltose, calcium stearate, silicon oxide, and shellac were used for test foods, and tablets having the same composition as the test foods except that an equivalent amount of dextrin was used instead of the casein enzymolysis product were used for placebo foods. An aqueous casein sodium solution is enzymolyzed with protease derived from *Bacillus licheniformis* and powdered to obtain the casein enzymolysis product contained in test foods, and the casein enzymolysis product contains LNDP. The casein enzymolysis product was added so that 0.6 mg per tablet of LNDP was contained in test foods.

Figure 9:
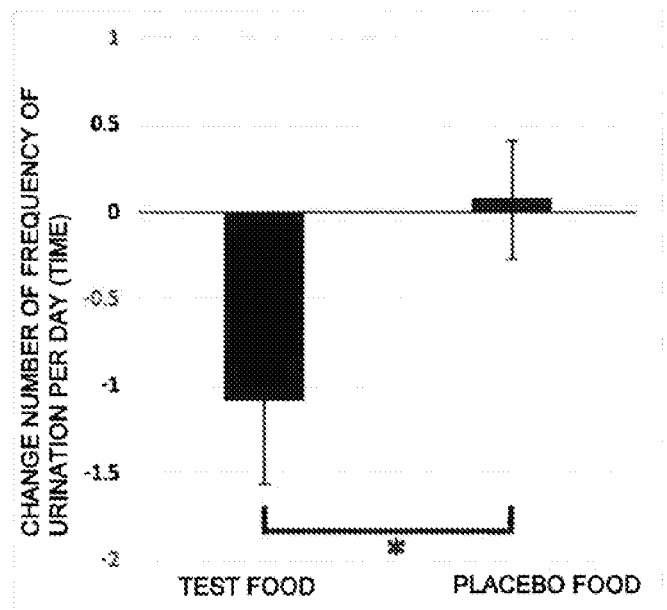
FIG. 9 is a graph relating to a change in the frequency of urination per day when a test food containing 2.4 mg of LNDP was ingested once after dinner (total LNDP 2.4 mg/day).

Consequently, the significant differences in the frequency of urination per day and the frequency of urination during the daytime awakening time (the daytime awakening time refers to awakening time from rising to retiring, and however, the time of awakening during sleep at night is excluded.) between the groups due to interaction were observed in the two-way analysis of variance. Furthermore, the significant improvement was observed in the amount of change in the frequency of urination per day from the first day of test meal ingestion to the fourteenth day of test meal ingestion (difference in the frequency of urination between the fourteenth day of test meal ingestion and the first day of test meal ingestion) between the groups in the signed rank sum test of Wilcoxon (FIG. 9). A pollakiuria improving effect of the ingestion of the test foods was observed from the above. Since there was no significant difference in the intake of water per day between both groups, it was considered that this effect was caused by LNDP.

Test Example 8 Pollakiuria Improving Effect (2)

Randomized, double-blinded, placebo-controlled, crossover, comparative study was performed on 12 subjects which are healthy men and women of ages of 40 or more and less than 65 with slight pollakiuria symptoms to examine the influence on the frequency of urination when LNDP is ingested a plurality of times per day. The test was performed using test foods containing LNDP and placebo foods not containing LNDP as test meals. Specifically, the 12 persons were divided into 2 groups each having 6 persons, and, in one group, the persons were made to ingest the test foods for 14 days and ingest placebo foods for 14 days after a 14-day washout period. In the other group, the persons were made to ingest the placebo foods for 14 days and ingest test foods for 14 days after a 14-day washout period. The tablets of Test Example 7 were used for test meals, and the test meal was ingested in a dosage of 4 tablets after lunch and dinner. Since the test foods contain 0.6 mg per tablet of LNDP, LNDP contained in a dose of test food is 2.4 mg, and the daily LNDP intake of a group which ingests test foods is 4.8 mg. The subjects were asked to write urination diaries recording the frequencies of urination and the urination times during the test period, and the influence of LNDP on the frequency of urination was evaluated using this.

Figure 10:
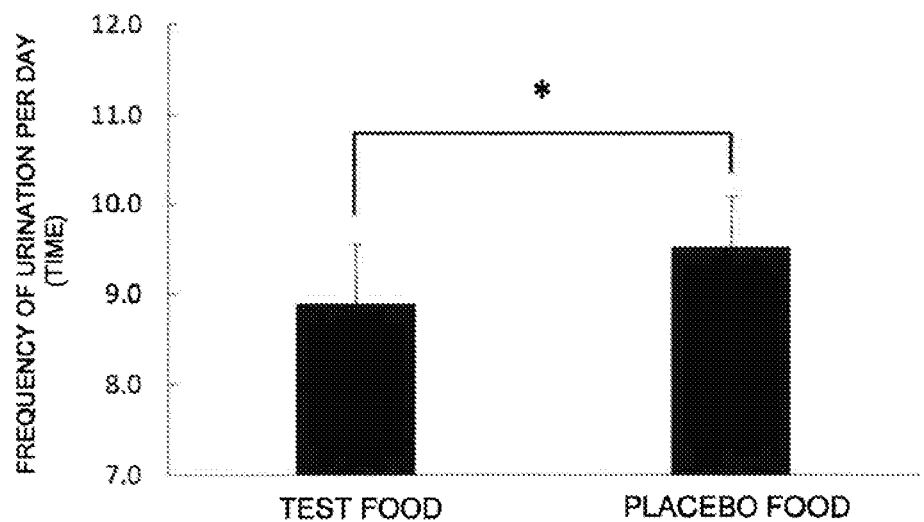
FIG. 10 is a graph relating to the frequency of urination per day when test food containing 2.4 mg of LNDP were ingested a total of twice including once after lunch and once after dinner (total LNDP 4.8 mg/day).
Figure 11:
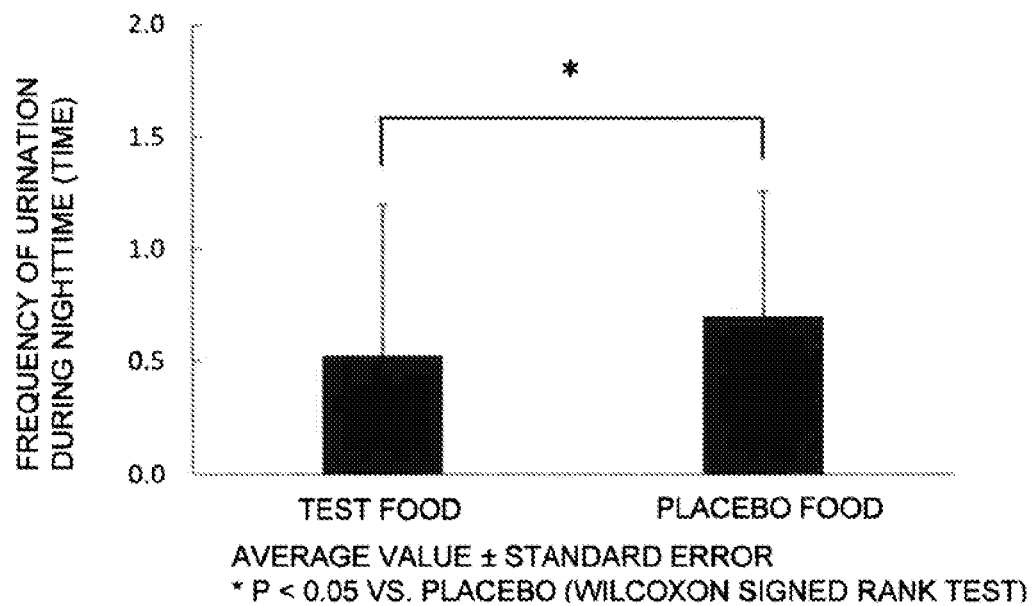
FIG. 11 is a graph relating to the frequency of urination during the nighttime when test food containing 2.4 mg of LNDP were ingested a total of twice including once after lunch and once after dinner (total LNDP 4.8 mg/day).
Figure 12:
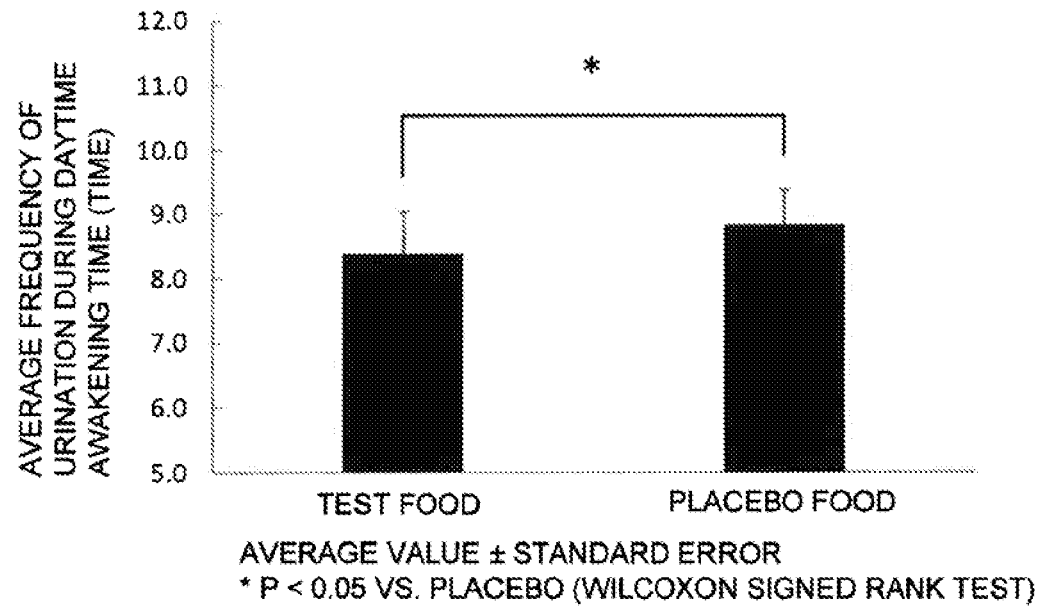
FIG. 12 is a graph relating to the frequency of urination during the daytime awakening time when test food containing 2.4 mg of LNDP were ingested a total of twice including once after lunch and once after dinner (total LNDP 4.8 mg/day).

Consequently, the significant differences in the main effects on the frequency of urination per day, the frequency of urination during the nighttime (the frequency of urination from retiring to rising), and the frequency of urination during the daytime awakening time between the groups were observed in the two-way analysis of variance. Furthermore, the significant improvement was also observed in the frequency of urination per day, the frequency of urination during the nighttime, and the frequency of urination during the daytime awakening time between the groups in the signed rank sum test of Wilcoxon (FIG. 10 to FIG. 12). The test food group specifically decreased in the frequency of urination per day, the frequency of urination during the nighttime, and the frequency of urination during the daytime awakening time by 0.65 times/day, 0.16 times/day, and 0.45 times/day on average, respectively, as compared with the placebo food group. Also, when the test foods were ingested a plurality of times per day, a pollakiuria improving effect was observed from the above. Since there was no significant difference in the intake of water per day between both groups, it was considered that this effect was caused by LNDP.

The invention claimed is:

1. A method for improving pollakiuria, comprising administering a composition comprising an effective amount of a peptide consisting of the amino acid sequence of Asn-Ile-Pro-Pro-Leu-Thr-Gln-Thr-Pro-Val-Val-Val-Pro-Pro-Phe-Leu-Gln-Pro-Glu SEQ ID NO: 1 or a salt thereof to a patient-in need of improving pollakiuria.

2. The method according to claim 1, wherein the peptide or a salt thereof is ingested by the patient in an amount of 0.001 mg to 1 g per day.

* * * * *